United States Patent [19]

Maria de Laat et al.

[11] Patent Number: 5,128,261

[45] Date of Patent: Jul. 7, 1992

[54] NATURAL DELTA-LACTONES AND PROCESS OF THE PRODUCTION THEREOF

[75] Inventors: Wilhelmus T. A. Maria de Laat, Zevenbergen; Peter H. van der Schaft, Leusden, both of Netherlands

[73] Assignee: PFW (Nederland) B.V., Amersfoort, Netherlands

[21] Appl. No.: 582,451

[22] Filed: Sep. 13, 1990

[30] Foreign Application Priority Data

Sep. 28, 1989 [EP] European Pat. Off. ........ 89202426.6

[51] Int. Cl.$^5$ .................. C12N 1/16; C12N 1/14; C12P 17/06; C12P 7/62; C12P 7/24

[52] U.S. Cl. ..................... 435/255; 435/125; 435/135; 435/147; 435/911

[58] Field of Search ............... 435/125, 135, 254, 255, 435/911, 147

[56] References Cited

U.S. PATENT DOCUMENTS

| | | | |
|---|---|---|---|
| 4,001,437 | 1/1977 | Jaeggi et al. | 426/41 |
| 4,020,185 | 4/1977 | Anderson et al. | 426/43 |
| 4,110,476 | 8/1978 | Rhodes | 426/41 |
| 4,289,788 | 9/1981 | Cajigas | 426/41 |
| 4,293,573 | 10/1981 | Bradley, Jr. et al. | 426/43 |
| 4,743,453 | 5/1988 | Ahern et al. | 426/43 |

OTHER PUBLICATIONS

Tahara et al., Agric. Biol. Chem, 39(1), pp. 281–282, 1975.

Scharpf et al., Biogeneration of Aromas, American Chemical Society, pp. 323–346, 1986.

*Primary Examiner*—Douglas W. Robinson
*Assistant Examiner*—Deborah K. Ware
*Attorney, Agent, or Firm*—David Edwards

[57] ABSTRACT

The present invention concerns natural 5-decanolide and 5-dodecanolide, obtainable by biocatalytic reduction of natural 2-decen-5-olide, respectively 2-dodecen-5-olide, as well as the production of natural 5-decanolide and 5-dodecanolide by biocatalytic reduction of the corresponding unsaturated natural 2-decen-5-olide, respectively 2-dodecen-5-olide.

9 Claims, No Drawings

NATURAL DELTA-LACTONES AND PROCESS OF THE PRODUCTION THEREOF

The present invention concerns natural delta-lactones, and the production thereof. More in particular the invention concerns natural 5-decanolide and 5-dodecanolide, and the production thereof using natural starting materials and biocatalysts.

In the use of flavoring compounds, it is often important that the flavor compound can be designated as "natural". In practice this means that the compound has been obtained by physical, enzymatic or microbiological processes from a product of plant or animal origin, in which products of petrochemical derivation are excluded.

Delta-lactones occur naturally in dairy products and are important constituents of dairy flavors. However, there is no natural 5-decanolide or 5-dodecanolide available by other routes than by expensive and uneconomical isolation from natural products such as butter. The use of these chemicals in natural flavors would require that both the production process and the substrates used in the process have the so-called natural status. Up to now no process has been disclosed for preparing natural delta-lactones.

In U.S. Pat. No. 3,076,750 the reduction of synthetic 5-oxo-acids with yeast is described. This process produces optically active delta-lactones in high concentrations, but these compounds cannot be considered as natural, because the starting materials are not natural.

There is a substantial amount of literature dealing with the production of natural gamma-lactones by means of fermentation processes using plant oils as precursor (Berger et al., 1986, Z. Naturforsch. 41c, 963-970; Farbood et al., 1983 U.S. Pat. No. W083/01072; Cheetham et al. 1988 European patent no. 0 258 993).

Cardillo et al. describe the conversion of $C_{14}-C_{19}$ gamma-hydroxy alkene fatty acids into $C_8$ and $C_{11}$ delta-lactones and $C_9$, $C_{10}$ and $C_{11}$ gamma-lactones in Cladiosporium suaveolens (Cardillo et al., 1989, J. Org. Chem. 54, 4979-4980). The substrates are known to be present in nature, but there is no readily available source.

The present invention is directed to natural 5-decanolide and natural 5-dodecanolide, obtainable by the biocatalytic reduction of the corresponding natural unsaturated 5-olides.

These flavoring compounds are novel products, as up to now there has not been a method for producing these flavoring compounds in a natural way, as defined hereinabove, and in a manner that is economically attractive. In the microbial hydrogenation of unsaturated 5-olides a person skilled in the art would expect that both the starting material and the product would be too toxic for microorganisms to be able to produce these products in sufficient amounts to be economically attractive. It has surprisingly been found that it is nevertheless possible to produce these products by microbial hydrogenation. More in particular it is possible to produce these 5-olides by the microbial hydrogenation of Massoi bark oil or fractions thereof, using yeasts or fungi.

It is known from literature, that baker's yeast can perform asymmetric reduction of C=O or C=C double bonds (Gramatica, 1988, Chim. Oggi, 6, 17-20). Baker's yeast is the biocatalyst most commonly used by synthetic chemists for stereoselective reduction of carbonyl compounds to optically active alcohols. Baker's yeast hydrogenation of the C=C double bond of alpha-beta unsaturated carbonyl compounds is a less extensively, but also well investigated reduction. (Davies et al. "Biotransformations in Preparative Organic Chemistry", Academic Press, 1989, p. 127-136). However, the biocatalytic hydrogenation of alpha-beta unsaturated lactones has not been described before.

The invention is also directed to a process for the preparation of natural 5-decanolide and natural 5-dodecanolide, comprising the biocatalytic reduction of the ring double bond of natural 2-decen-1,5-olide and natural 2-dodecen-1,5-olide, using yeast strains such as Saccharomyces cerevisiae or imperfect fungi.

The two flavor compounds are obtained by the process in high yields. As indicated hereinabove this is quite unexpected in view of the properties of the starting material and the products.

In the process of the invention yeast species or fungal species can be used. Preferred species are Saccharomyces cerevisiae, Polyporus durus, Ischnoderma benoinum, Bjerkandera adusta, Poria xantha and Pleurotus ostreatus.

A preferred microorganism is baker's yeast, as this gives good yields, whereas it is very easily obtainable.

The process can be carried out in a conventional way for biocatalytic reactions. It is possible to use the biocatalyst, i.e. the microorganism or the enzyme obtained from the microorganism, either in free form or in immobilized form.

A cosubstrate such as glucose is preferably present in the system in order to regenerate the cofactors that are used during the bioreduction. A nitrogen source, minerals, vitamins and other additives may be present for the maintenance of the biocatalyst. According to a preferred embodiment also organic solvents or adsorbents such as resins or other clathrating agents can be present, to circumvent the toxicity of the substrate and/or product towards the biocatalyst.

The yeasts and fungi disclosed herein are able to produce natural 5-olides using Massoi bark oil as a substrate, but there is no criticality in the use of these strains and other strains among the yeasts and fungi.

Commercial baker's yeast or the other strains can be suspended in 50 mM phosphate buffer at a pH of about 2.5 to 7.0, preferably 3.0 to 6.0 at a final concentration of about 10 to 1500 g/l wet weight, preferably 50 to 250 g/l. In the preferred embodiment of the process about 0.001 to 25%, preferably 0.01 to 2.5% of any organic cosubstrate preferably a sugar, more preferably glucose, is added to the bioconversion buffer for regeneration of reduction equivalents which are needed for the enzymatic reduction.

To avoid substrate inhibition of the reaction rate and toxicity of the substrate towards the biocatalyst, the substrate is preferably added stepwise or continuously to the cell suspension at a rate which allows that the total concentration of the unsaturated lactones never exceeds the preferred concentrations of 0.2 g/l.

Additionally organic solvents, such as heptane and octane, organic resins, such as Amberlite XAD and other clathrating agents, such as cyclodextrins can be added to the reaction mixture to prevent inhibition.

The bioconversion can be carried out in a stirred tank or fermentor at about 100 to 1000 RPM, preferably at 150 to 400 RPM. The temperature is maintained at about 15° to 37° C., preferably at 27° to 35° C., throughout the process.

After the reaction is completed (99% conversion) the broth can be filtered and the biocatalyst can be washed with buffer. The filtrate and wash buffer are collected and can be extracted with an organic solvent such as pentane/dichloromethane 2:1. The extract can be dried, for example over anhydrous $Na_2SO_4$ and the products can subsequently be obtained by distilling off the solvent. Analysis of the extracts was performed by GLC. The purity of the products can be 99% with a yield of 90% based on the bark oil or pure unsaturated lactones added during the process.

Examples of the method will now be given to illustrate but not to limit the invention.

EXAMPLE 1

*Saccharomyces cerevisiae* is incubated at pH 5.0 in the presence of 2.5% glucose and 0.100 g/l 2-decen-1,5-olide. The bioconversion is carried out at 30° C. and 100 RPM at a biomass concentration of 9.5 g/l dry weight. After two hours of incubation the yield of 5-decanolide is 0.090 g/l (90%).

EXAMPLE 2

*Saccharomyces cerevisiae* is incubated in an aerated fermenter at a concentration of 15.0 g/l dry weight in phosphate buffer at pH 5.5 under continuous addition of glucose (15 g/l hr.). The bioconversion process is carried out at 35° C. and 500 RPM while 2-decen-1,5-olide is added stepwise at 0.1 g/l hr. After 16 hours of incubation the yield of 5-decanolide is 1.41 g/l (88%).

EXAMPLE 3

As Example 2, except that the incubation is carried out in the presence of 2% cyclodextrin and 2-decen-1,5-olide is added at 0.2 g/l hr. After 8 hours of incubation the yield of 5-decanolide is 1.25 g/l (78%).

EXAMPLE 4

As Example 1, except that 5% heptane is added to the bioconversion mixture and the concentration of 2-decen-1,5-olide is 0.200 g/l. After four hours of incubation the yield of 5-decanolide is 0.088 g/l (44%).

EXAMPLE 5

*Polyporus durus* (CBS 313.36) maintained on a malt extract agar slant is cultured on a nutrient medium containing 3% glucose, 0.45% asparagine, 0.1% $MgSO_4.7H_2O$, 0.15% $KH_2PO_4$, 0.005% thiamine, 1% of a triglyceride, preferably soya oil or miglyol and trace elements $FeCl_2$, $FeSO_4$, $MnSO_4$, $CuCl_2$, all 5 mg/l and $CaCl_2$, $ZnCl_2$ 2 mg/l. The initial pH of the medium is 6.0. Culturing is carried out in an incubator shaker stirring 300 ml erlenmeier flasks containing 100 ml medium at 200 RPM and at 28° C. The cells are harvested after 10 days of growth. The collected mycelium is incubated at pH 3.0 in the presence of 2.5% glucose and 0.140 g/l 2-decen-1,5-olide. The bioconversion was carried out at 30° C. and 100 RPM at a biomass concentration of 60 g/l wet weight. After 6 hours of incubation the yield of 5-decanolide is 0.122 g/l (87%).

EXAMPLE 6

As Example 5 except that culturing is carried out for 7 days. The collected mycelium is resuspended at a concentration of 100 g/l wet weight in phosphate buffer at pH 4.0 containing 2.5% glucose. The bioconversion process is carried out at 30° C. and 100 RPM while 2-decen-1,5-olide is added in three steps of 0.140 g/l at intervals of 2 hours. After six hours of incubation the yield of 5-decanolide is 0.412 g/l (87%).

EXAMPLE 7

As Example 6, except that the crude Massoi bark oil is used as the substrate in 4 portions of 0.100 g/l added at intervals of two hours. After 8 hours the concentrations of 5-decanolide and 5-dodecanolide are 0.324 g/l and 0.02 g/l respectively. The yield of saturated 5-olides is 95%.

EXAMPLE 8

As example 6, except that 200 g/l biomass was used and 2-decen-1,5-olide was added stepwise in four portions of 0.100 g/l at intervals of one hour. After 4 hours the mycelium is collected, washed and incubated again for another 3 hours with three times stepwise addition of 2-decen-1,5-olide at the same rate as before. The process yields 0.222 and 0.578 g/l 5-decanolide after 4 and 7 hours respectively (yield: 83% 5-decanolide).

EXAMPLE 9

*Ischnoderma benzoinum* (CBS 311.19) is cultured as in Example 5 for 21 days. The collected mycelium is used in a bioreduction process as in Example 5 at a biomass concentration of 20 g/l wet weight and in the presence of 0.100 g/l 2-decen-1,5-olide. After 3 hours 0.021 g/l 5-decanolide is produced (yield: 21% 5-decanolide).

EXAMPLE 10

*Bjerkandera adusta* (CBS 595.78) is cultured as in Example 5 for 30 days. The collected mycelium is used in the bioreduction process as in Example 5 at a biomass concentration of 20 g/l wet weight and in the presence of 0.100 g/l 2-decen-1,5-olide. After 3.75 hours 0.097 g/l 5-decanolide is produced (yield: 97% 5-decanolide).

EXAMPLE 11

*Poria xantha* (CBS 332.29) is cultured as in Example 5 for 30 days. The collected mycelium is used in the bioreduction process as in Example 5 at a biomass concentration of 20 g/l wet weight and in the presence of 0.100 g/l 2-decen-1,5-olide. After 5 hours 0.015 g/l 5-decanolide is produced (yield: 15% 5-decanolide).

EXAMPLE 12

*Pleurotus ostreatus* (CBS 411.71) is cultured as in Example 5 for 30 days. The collected mycelium is used in the bioreduction process as in Example 5 at a biomass concentration of 20 g/l wet weight and in the presence of 0.100 g/l 2-decen-1,5-olide. After 4.75 hours 0.023 g/l 5-decanolide is produced (yield: 23% 5-decanolide).

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. Process for the preparation of natural 5-decanolide and natural 5-dodecanolide, comprising biocatalytic reducing the ring double bond of a substrate of natural 2-decen-1,5-olide and natural 2-dodecen-1,5-olide, using a yeast or a fungus species selected from the strains consisting of *Saccharomyces cerevisiae*, *Polyporus durus*,

*Ischnoderma benzoinum, Bjerkandera adusta, Poria xantha*, and *Pleurotus ostreatus*, and recovering the 5-decanolide and natural 5-dodecanolide compounds.

2. Process according to claim 1, wherein the yeast species is *Saccharomyces cerevisiae*.

3. Process according to claim 1, wherein the fungus species is *Polyporus durus* (CBS 313.36), *Ischnoderma benzoinum* (CBS 311.29), *Bjerkandera adusta* (CBS 595.78), *Poria xantha* (CBS 332.29) or *Pleurotus ostreatus* (CBS 411.71).

4. Process according to claims 1, 2 or 3, wherein the substrate is added stepwise or continuously.

5. Process according to claim 3, wherein the biocatalytic reducing step is carried out in the precense of a sugar as a cosubstrate.

6. Process according to claim 5, wherein the cosubstrate is added stepwise or continuously.

7. Process according to claim 6, wherein the biocatalysis is carried out in the presence of an organic solvent, an organic resin or other clathrating agent.

8. Process according to claim 7, wherein the clathrating agent is a cyclodextrin.

9. The process according to claim 8, wherein the biocatalyst is used in immobilized form.

* * * * *